United States Patent [19]

Rosevear

[11] 4,425,434
[45] * Jan. 10, 1984

[54] IMMOBILIZATION OF BIOLOGICALLY ACTIVE SUBSTANCES

[75] Inventor: Alan Rosevear, London, England

[73] Assignee: United Kingdom Atomic Energy Authority, London, England

[*] Notice: The portion of the term of this patent subsequent to Apr. 6, 1999 has been disclaimed.

[21] Appl. No.: 291,958

[22] Filed: Aug. 11, 1981

Related U.S. Application Data

[63] Continuation-in-part of Ser. No. 15,405, Feb. 26, 1979, Pat. No. 4,323,650, which is a continuation of Ser. No. 773,157, May 1, 1977, abandoned, which is a continuation of Ser. No. 587,201, Jun. 16, 1975, abandoned.

[30] Foreign Application Priority Data

Jun. 25, 1974 [GB] United Kingdom ............... 28212/74

[51] Int. Cl.³ .................... C12N 11/14; C12N 11/06; C12N 11/04
[52] U.S. Cl. .................................. 435/176; 435/181; 435/182
[58] Field of Search ............... 435/174, 177, 176, 178, 435/180, 181, 182

[56] References Cited

U.S. PATENT DOCUMENTS

| | | | |
|---|---|---|---|
| 3,736,231 | 5/1973 | Stanley et al. | 435/177 |
| 3,804,719 | 4/1974 | Messing | 435/176 |
| 3,838,007 | 9/1974 | Van Velzen | 435/182 X |
| 4,182,655 | 1/1980 | Hartmeier | 435/181 |
| 4,323,650 | 4/1982 | Roserear | 435/176 X |

OTHER PUBLICATIONS

Olson et al., Immobilized Enzymes in Food and Microbial Processes, Plenum Press, N.Y., 1974 (pp. 54–61).

*Primary Examiner*—David M. Nafe
*Attorney, Agent, or Firm*—Larson and Taylor

[57] ABSTRACT

The invention relates to a method for the preparation of discrete particles containing a biologically active substance comprising discrete particles of support material having immobilized in the pores thereof a biologically active substance (e.g. an enzyme). The method includes precipitating a biologically active substance in the pores of the particles of support material, by use of a precipitating agent comprising or including a water miscible organic liquid, and treating the biologically active substance precipitated in the pores to cause cross-linking so as to immobilize biologically active substance in the pores of the particles or porous support material.

11 Claims, No Drawings

IMMOBILIZATION OF BIOLOGICALLY ACTIVE SUBSTANCES

This application is a continuation-in-part of application Ser. No. 15,405, filed Feb. 26, 1979, now U.S. Pat. No. 4,323,650, which is a continuation of application Ser. No. 773,157, field May 1, 1977, now abandoned which is a continuation of application Ser. No. 587,201, filed June 16, 1975, now abandoned.

The present invention relates to the immobilization of biologically active substances, for example, enzymes, in a support material.

Biologically active substances, such as enzymes, are useful as catalysts in certain processes (e.g. amyloglucosidase in the production of glucose from starch). However, often in practice it is found that biologically active substances are available only in forms, such as enzyme preparations, which are water soluble. This means that such a substance cannot be economically isolated at the end of a process with the result that the substance is either lost in the spent liquor or contaminates the product.

Therefore it can be advantageous to immobilize a biologically active substance on a support material so that it can be separated from reaction media by physical techniques such as filtration or sedimentation. In addition biologically active substances immobilized on a support material are available for "localised" use, e.g. as a bed in a column.

A biologically active substance is considered to be immobilized on a support material if it is fixed thereon in such a manner that permits at least a major proportion of the substance to be retained by the support material under the particular process conditions in which the support material and biologically active substance are used.

Various methods for "fixing" or "immobilizing" (often referred to as "insolubilising") biologically active substances on support materials have previously been proposed in the art. However, these methods are unsatisfactory in that their products suffer from disadvantages. For example, the biologically active substance is either "leached" from the support material when in use and/or the physical, chemical or microbiological stability of the substance/support material combination is unsatisfactory with the result that the substance is not available for continued re-use over prolonged periods of time.

According to one aspect of the present invention there is provided a method for the preparation of discrete particles containing a biologically active substance, comprising discrete particles of porous support material having a biologically active substance immobilized in the pores thereof, which method comprises selecting discrete particles of a porous support material having a pore size and structure that permits entry of a solution containing biologically active substance, said particles also being selected to have a particle size suitable for use in a column or fluidised bed reactor, introducing a solution containing biologically active substance into the pores of said particles of porous support material substantially to fill the pore volume of said particles of porous support material, treating the solution introduced into the pores with a precipitating agent to precipitate said biologically active substance so as to retain said biologically active substance in the pores of the particles of porous support material and thereby hold the biologically active substance available for cross-linking, said precipitating agent comprising a water miscible organic liquid or including a water miscible organic liquid for improving the precipitation, cross-linking the biologically active substance precipitated in the pores of the porous support material so as to immobilize biologically active substance in the pores of the particles of porous support material, said introduction of solution containing biologically active substance and said precipitating and cross-linking being conducted so as to provide a major proportion of the immobilized biologically active substance in the pores of, rather than on the external surface of, the particles of porous support material and removing surplus precipitated and cross-linked biologically active substance outside of the particles if required.

The term "biologically active substance" as used in this specification embraces proteinaceous substances (e.g. enzymes), and includes substances which are biologically active per se and those which are not, but which can be activated after immobilization to make them biologically active. In the latter case a biologically active substance can be treated with an inhibitor to deactivate it, immobilised and then reactivated (e.g. inactive mercuripapain can be immobilised and subsequently activated by use of EDTA to remove mercury).

By "proteinaceous substances" we mean to embrace proteins per se and substances having a proteinaceous component (e.g. glyco-proteins (such as amyloglucosidase) and lipo-proteins.

Furthermore, it is to be understood that the term "biologically active substance" embraces inter alia those substances capable of participating in specific interactions, such substances including, for example, substances of biological origin and those which act on living organisms. Substances of synthetic origin which can participate in reactions involving specific interactions analogous to those which can occur with naturally occurring substances are also embraced within the term "biologically active substance".

In immobilising a biologically active substance in accordance with the present invention the substance is precipitated and thereby retained in the pores of the particles of support material so that a substantial concentration of the substance is available to be immobilized therein by cross-linking. Whilst anzyme-containing organic gels have been prepared previously (e.g. by precipitation and cross-linking), optionally mixed with the diatomaceous filter aid available under the Trade Name "Celite", they have tended to exhibit properties which have reduced their practical value. Thus such gels have tended to be weak and compressible and, consequently have given rise to difficulties in column and fluidised bed use (e.g. by compaction in column use resulting in a build-up of back pressure).

Previously prepared enzyme-containing organic gels mixed with "Celite" as mentioned in the immediately preceding paragraph have been composed of fine particles of filter aid and large regions of compressible organic gel. The literature reports that the enzyme-containing organic gels (even when mixed with "Celite") gave rise to difficulties in column use due to packing together causing back pressure build-up in the column. It is also reported that up flow operation was equally difficult since the fineness and density of the particles permited them to move upwards and pack against the upper column support (Olson et al: "Immobilized Enzymes in Food and Microbial Processes" page 55—Plenum Press New York).

In accordance with the present invention the biologically active substance is protected within each of the discrete particles of support material which particles are selected to be sufficiently mechanically robust for the intended use (e.g. in a column or fluidised bed).

Furthermore in accordance with the present invention positive steps are taken to avoid the formation of "surplus" precipitated and cross-linked biologically active substance outside or around the particles of support material. Any such "surplus" is removed in accordance with the present invention if required. It will be understood that "surplus" precipitated and cross-linked biologically active substance is that which is not securely enmeshed with the support material and can thus be easily separated (e.g. by washing).

It will also be understood that the cross-linking with which the present invention is concerned is within the biologically active substance itself and that any cross-linking between the substance and the support material is coincidental. The cross-linking of the substance within itself renders it entrapped and enmeshed within the pores.

The selection of particle size is made on practical grounds depending upon the particular conditions prevailing for example column or bed size, flow rate, back pressure which can be tolerate and reaction rate of the chosen immobilized biologically active substance when in use performing a chosen reaction.

In general the lower limit of size will be determined for packed bed column use by the back-pressure which can be tolerated and typically sizes of $<100$ μm diameter may present difficulties.

Also, in general, the upper particle size limit will be determined by the diffusion rate of reactants within the immobilized biologically active substance in the support material. Clearly the larger the particle the larger the diffusion paths within it and typically on size of $>5$ mm could begin to make the rate of reactant diffusion the rate determining step.

To reduce the spread of residence time of species with which the immobilized biologically active substance is to interact in use it is also preferred that the particle size uniformity is $\pm 50\%$.

It has been found in accordance with the present invention that improved precipitation can be achieved by use of a precipitating agent which comprises or includes a water miscible organic liquid capable of enhancing the ability of the biologically active substance to agglomerate during precipitation. Precipitation using wholly aqueous reagents gives rise to a finely divided precipitate. The use of a water miscible organic liquid in accordance with the present invention (e.g. acetone) promotes the precipitation of biologically active substance in a 'sticky' or adherent form which is gelatinous and tends to clump readily to form an agglomerated precipitate.

By way of example, it has been found that a 20% improvement in immobilized enzyme actively retained on the porous support material can be achieved by using a miscible organic liquid in accordance with the present invention.

It is believed that the enhancement of the ability to precipitate in an agglomerated form leads to an improved retention of the biologically active substance in the support material during precipitation and reduces the tendency of the substance to diffuse out during the completion of precipitation and the effecting of cross-linking.

Although a portion of biologically active substance can be immobilized on the outer surface of a support material, in accordance with the present invention, the pores of a porous support material are utilised, since in this way, the surface area/volume ratio of the support material is greatly increased and thus a greater amount of biologically active substance immobilized. It will be appreciated that in addition to being such as will permit entry of the substance to be immobilized the pore size and pore structure of the porous support material should also be such as to permit in use, the entry of species with which the immobilized substance is to interact. Further, it is to be understood that the precipitated and cross-linked biologically active substance, which extends three-dimensionally in the pores of the porous support material, is permeable so as to permit, in use, the permeation of species with which it is to interact and the release of any products.

By using a porous support material and a biologically active substance which can enter the pores thereof, the method of the present invention enables biologically active substance to be immobilized in the pores of a porous support material. Thus, after precipitation and cross-linking, biologically active substance immobilized in the pores of the porous support material will be present in the pores of the material although some may be present upon its outer surface. Thus in accordance with the present invention a major proportion of the immobilized substance will be present in the pores rather than on the external surface of the particulate porous support material.

According to another aspect of the present invention there is provided a support material having immobilized thereon a biologically active substance whenever prepared by a method in accordance with the invention.

In accordance with one particular embodiment of the invention the precipitation and cross-linking processes are carried out sequentially by treating biologically active substance, previously introduced into the pores of a porous support material, with a precipitating agent and then a cross-linking agent to cross-link the biologically active substance.

It has been found that it is possible to treat some biologically active substances with a precipitating agent and a cross-linking agent simultaneously. This is possible, for example, in the case of those anzymes (e.g. amyloglucosidase) where the time taken for cross-linking to occur far exceeds the time taken to precipitate the enzyme.

In carrying out the present invention preferably particles of a porous support material are first soaked in a concentrated solution of biologically active substance (e.g. an enzyme) and then are subsequently treated with the precipitating agent, which does not denature the substance, to precipitate biologically active substance in the pores of the porous particles of support material and a cross-linking agent to cross-link and thereby immobilize the substance in the pores of the particles of porous support material.

Freeze drying may be used in conjunction with precipitation and cross-linking in carrying out the present invention.

Thus in accordance with another embodiment of the present invention particles of porous support material are soaked in a concentrated solution of biologically active substance (e.g. an enzyme), biologically active substance is retained in the particles of porous support material by freeze-drying, further biologically active substance is introduced into the pores of the particles by immersion in a concentrated solution of biologically active substance and precipitated by use of a precipitating agent, and the biologically active substance which has been retained in the pores by freeze drying and precipitation is treated with a cross-linking agent under conditions such that substantially no retained substance goes into solution, to effect cross-linking and immobilization of the substance in pores of the particles of support material.

It will be appreciated that when carrying out the method of the present invention biologically active substance is introduced, in solution, so as to fill the pore volume of the material and then treated with a precipitation agent, in such a way that significant amounts of the substance are not displaced from the pores, to cause precipitation of the substance and retain the substance in the pores of support material. The precipitated substance, which is "localised" in the support material, is subsequently cross-linked to immobilize it in the pores.

Using the method of the present invention amyloglucosidase has been immobilized, using tannic acid and acetone as a precipitating agent and glutaraldehyde as a cross-linking agent, on the following inorganic materials which are given by way of example:

porous titania spheroids, porous calcium phosphate spheroids, porous alumina spheroids, porous zirconia spheroids, controlled pore glass (Corning glass types CPG10-240; 10-370; 10-1250; 30-370 and 30-2000), crushed thermalite block, Laporte Spent Catalyst, Crosfield Spent Catalyst (Laporte and Crosfield Spent Catalysts contain porous alumino-silicate particles). It is to be understood that materials other than the foregoing examples are suitable for use as support materials. For example, enzymes have been immobilized in accordance with the present invention on support materials comprising porous spheroids fabricated from porous natural diatomaceous earths such as Kieselguhr and that available under the Trade Name 'Celite'. Furthermore, certain organic materials such as wood, may be used as support materials. For example, amyloglucosidase has been immobilized on wood chips using tannic acid and acetone as a precipitating agent and glutaraldehyde as a cross-linking agent. Very desirably the support material should be substantially insoluble under the process conditions and in the reaction media in which the support material and biologically active substance are used. The following are examples of biologically active substances which have been immobilized on porous titania spheriods (having a particle size of 500μ diameter and 60% of the pores in the range 2700–10,000 Å diameter) using tannic acid and acetone as precipitating agent and glutaraldehyde as cross-linking agent: amyloglucosidase (four types), lactase (four types), α-amalyse, chymotrypsin, trypsin, urease, glucose oxidase, lipoxidase, glucose isomerase, papain, neutrase and pronase.

More than one biologically active substance can be immobilized on the same support in accordance with the present invention. Thus, amyloglucosidase and α-amylase have been immobilized together.

A number of different reagents have been used as the precipitating agent in carrying out the method of the present invention. Thus, using glutaraldehyde as the cross-linking agent a commercially available amyloglucosidase (available under the name "Agidex") has been immobilized on porous titania spheriods (particle size and pore size as hereinbefore stated) using the following examples of precipitating agents: tannic acid in 70% ethanol, tannic acid in 50% acetone, tannic acid in 2:1 water/isopropanol, synthetic polyphenols in 50% acetone (available under the names Tannia, Fixoflex, Fixin, Hysolad from Harshaw Chemicals Ltd.).

Amyloglucosidase (Agidex) has also been immobilized in accordance with the present invention on porous titania spheriods (particle and pore size as hereinbefore stated) using formaldehyde as the cross-linking agent and tannic acid and acetone as precipitating agent and, additionally, using diethylpyrocarbonate as a cross-linking agent and tannic acid in 70% ethanol as precipitating agent. Glyoxal and bis-diazonium salt have also been used as a cross-linking agent in accordance with the present invention. Also, in accordance with the present invention glucose oxidase has been immobilized on tiania spheriods using tannic acid and acetone as precipitating agent and diethylpyrocarbonate as cross-linking agent, and papain has been immobilized on titania spheroids using tannic acid and acetone and formaldehyde.

The optimum conditions for immobilizing biologically active substances in accordance with the present invention are, at least in part, dependent upon the biochemical properties of the substance. Thus, the choice of, for example, precipitating agent, cross-liking agent and cross-linking time is optimised by experiment.

The time for immobilization can vary between say ½ hour to 24 hours depending on the biologically active substance.

The method of the present invention is preferably carried out at about 4° C. It has been noted that inactivation of certain biologically active substances can occur at higher temperatures. However, this depends on the substance and higher or lower temperatures could be appropriate.

It has been found that when immobilizing amylglucosidase (Agidex) on porous titania spheriods (particle size and pore size as hereinbefore stated) by precipitation and cross-linking, the best performance from the point of view of enzyme activity of the immobilized enzyme is obtained by using tannic acid in acetone as the precipitating agent and glutaraldehyde as the cross-linking agent. For example, it has been found that using this particular combination of precipitating agent and cross-linking agent and apparent enzyme activity of amyloglucosidase (Agidex) immobilized on porous titania spheriods can be up to 20% of the enzyme activity of the aqueous enzyme preparation used as the source of amyloglucosidase. Using 5% tannic acid in 5:1 acetone/water as a precipitating agent and gluteraldehyde as the cross-linking agent a batch of amyloglucosidase immobilized on porous titania spheriods (particle size and pore size as hereinbefore stated) was prepared from ~110 g titania spheriods and 30 ml Agidex, and packed into a column, 60 cm high and 100 mls in volume, to form a bed.

An acid thinned starch solution was passed through the column at a rate of between 52 and 230 ml/hr. The column was maintained at 60° for 8 days during which 9 liters of the solution were treated.

The Dextrose Equivalent (D.E.) of the product from the column was as high as that expected when a soluble enzyme is used for the same conversion process. The degree of hydrolysis of the product was constant during 7 days of steady use of the column.

A column of amyloglucosidase immobilized on porous titania spheriods was used continuously to hydrolyse a dextrin solution over a period of 7½ days. The product from the column had a constant D.E. value which indicated almost total conversion of the starting material. Subsequently, the column was washed free of dextrin solution, was stored for 5 weeks at room temperature and was re-used for the same hydrolysis process. The D.E. of the product was found to be the same as that obtained previously. The column was stored for a further 11 weeks and it was found that there was no serious loss in the enzyme activity.

It has been found that titania spheriods having amyloglucosidase immobilized thereon in accordance with the present invention may be used in either a packed bed, as described above, in a fluidised bed reactor or in a stirred tank reactor. Amyloglucosidase has been immobilized on porous titania spheroids (particle size and pore size as hereinbefore stated) using freeze drying and a precipitating agent to effect temporary retention and gluteraldehyde to cause cross-linking.

Enzymes have been immobilized in situ on a column of porous titania spheroids.

During in situ immobilization excess biologically active substance not temporarily retained on the support material can be reclaimed for recycling by washing the support material (e.g. with acetone/tannic acid) prior to cross-linking.

Spent immobilized enzyme has been removed from titania spheriods and the spheriods re-used for further immobilization. Concentrated nitric acid, concentrated caustic soda or heating in a furnace were suitable for removing enzyme from the spheriods.

A wide range of biologically active substances can be immobilized on a wide range of support materials in accordance with the present invention. Consequently, the invention offers the advantage of flexibility over known "immobilization" methods in that a support material can be chosen from a wide range of materials, on the basis of its properties, to suit a particular application.

The present invention will now be illustrated by reference to the following Examples (in which Examples 1 to 12 inclusive are Examples in accordance with the invention and Example 13 is a comparative Example):

EXAMPLE 1

Agidex solution (1 ml) was added to porous titania spheriods (3 ml; 500μ particles size and having 60% of the pores in the range 2700–10000 Å diameter), on an ice bath and was allowed to distribute throughout the spheriods. A 5% solution of tannic acid in 5:1 acetone:water (1.5 ml), previously cooled on an ice bath, was added followed by a 50% aqueous solution of gluteraldehyde (0.25 ml). The liquid level was then just above the surface of the porous titania spheriods. After 5 hours the spheriods were removed from the ice bath, washed and packed into a column so that the enzyme activity could be investigated. A solution of dextrin was used to investigate the properties of the column and, taking the activity of the original Agidex solution as 100%, the apparent activity of the immobilized enzyme in the column was found to be 20%.

EXAMPLE 2

Agidex solution (4.5 ml) was distributed throughout porous titania spheriods (15 ml) as in Example 1. A cooled 2% solution of tannic acid in acetone (6.75 ml), into which a 50% aqueous solution of glutaraldehyde (1.05 ml) had recently been mixed, was added and the resulting stiff slurry was thoroughly mixed. After 5 hours the spheroids were washed and the enzyme activity assayed as in Example 1. The apparent enzyme activity of the immobilized enzyme was found to be similar to that obtained in Example 1.

EXAMPLE 3

Agidex solution, diluted 1:1 with water (8 ml) was distributed throughout porous titania spheroids (10 ml; particle size and pore size as in Example 1) and was freeze-dried (lyophilised). Agidex solution (1.5 ml) was distributed throughout 5 ml of these lyophilised spheroids and a cooled 2% solution of tannic acid in acetone (2.25 ml) and 50% glutaraldehyde (0.35 ml) were added in the same way as in Example 2. The apparent activity of the immobilized enzyme was found to be 15% more than the activity of immobilized enzyme prepared using porous titania spheroids, but no freeze-drying step.

EXAMPLE 4

Agidex solution (2 ml) was added to, and distributed throughout, 5 mls of porous glass particles (Corning CPG 10-1250, 36–75μ particle size) on an ice bath. A cooled 5% solution of tannic acid in 5:1 acetone:water (3 ml) was added followed by a 50% aqueous solution of glutaraldehyde (0.5 ml). After 5 hours the glass particles were washed and the enzyme activity investigated in a small stirred batch reactor. The apparent activity of the immobilized enzyme was 93% of the activity of enzyme immobilized on porous titania spheroids of the type used in Examples 1, 2 and 3.

EXAMPLE 5

Agidex solution (1 ml) was distributed throughout porous titania spheroids (3 ml) as in Example 1. 1.5 mls of a cooled 10% solution of Fixoflex (a synthetic polyphenol) in 5:1 acetone:water was added followed by a 50% aqueous solution of glutaraldehyde (0.25 ml). After 5 hours the spheroids were washed and when the immobilized enzyme was assayed as in Example 1 it was found to have 82% of the activity of immobilized enzyme prepared with tannic acid in an acetone:water mixture as the precipitating agent.

EXAMPLE 6

1 ml of an aqueous solution of lactase (Maxilact 75 mg/ml) was added to and distributed throughout 3 mls of porous titania spheroids. A cooled 0.25% solution of tannic acid in 5:1 acetone:water (1.5 ml) was added followed by a 20% aqueous solution of glutaraldehyde (0.1 ml). After 20 minutes the spheroids were washed and packed into a column. The apparent activity of the immobilized enzyme was 11% of the activity of the soluble enzyme when o-nitro phenyl-β-D galactoside was used as the substrate.

EXAMPLE 7

Agidex solution (1.5 ml) was added to porous titania spheroids (500μ; 5 ml) on an ice bath and distributed throughout the spheroids. A cooled 2% solution of tannic acid in acetone (2.25 ml) was added followed by a 37% aqueous solution of formaldehyde (0.35 ml). After 5 hours the spheroids were washed and the immobilized enzyme was assayed as in Example 1. It was found to have an enzyme activity which was 56% of that of a similar immobilized enzyme prepared using glutaraldehyde as the cross-linking agent.

EXAMPLE 8

Agidex (1 ml) was distributed throughout a wad of soft wood chips, which occupied a volume of 3 mls, on an ice bath. A cooled 2% solution of tannic acid in acetone (1.5 ml) into which a 50% aqueous solution of glutaraldehyde (0.25 ml) had recently been mixed, was added and the reagents were thoroughly mixed. After 5 hours the chips were washed and loosely packed into a small column to enable the enzyme activity to be assayed as in Example 1. The chips had an enzymic activity which as 74% of the activity of the immobilized enzyme in Example 2.

EXAMPLE 9

An aqueous solution of glucose isomerase enzyme (1.5 ml obtained by aqueous extraction of Maxazyme-GI 14,000 cells) was allowed to soak into 5 g of porous titania spheroids (particle size of 500μ diameter and 60% of the pores in the range 2,700–10,000 Å diameter) on an ice bath. The enzyme was precipitated and cross-linked by means of a solution of 3% tannic acid in acetone (2.25 ml) and 50% aqueous glutaraldehyde (0.05 ml).

After reacting for 1½ hours on an ice bath the spheroids were washed and the enzyme activity assayed.

It was found that the spheroids contained 35% of the enzyme activity present in the starting solution of the enzyme.

EXAMPLE 10

A solution of α-chymotrypsin and bovine serum albumin (20 mg/ml and 50 mg/ml respectively; 3 ml) was soaked into porous titania spheroids (355–500μ; 10 ml) and the spheroids then placed on an ice bath. A pre-cooled, freshly prepared solution of 4% w/v tannic acid in 3:1 v/v ethanol/water 5 ml) containing glutaraldehyde (7.5 μl/ml) was added to precipitate the proteins and the resulting mixture was left for 1½ hours on an ice bath to effect cross-linking. The spheroids were washed free of loosely bound gel material using water and tyrosine ester substrate solution. On repeated assay with tyrosine ethyl ester solution the spheroids were found to have α-chymotrypsin activity.

EXAMPLE 11

A solution of pronase (10 mg/ml, 3 ml) was soaked into porous titania spheroids (355–500μ; 10 ml) and the spheroids then placed on an ice bath. A pre-cooled, freshly prepared solution of 1% tannic acid in 3:1 v/v ethanol/water (5 ml) containing glutaraldehyde (7.5 μl/ml) was added to precipitate the enzyme and the resulting mixture left for 2 hours on an ice bath to effect cross-linking. The spheroids were washed free of loosely bound gel material using water and tyrosine ester substrate solution. On repeated assay with tyrosine ethyl ester solution, the spheroids were found to have pronase activity.

EXAMPLE 12

1.5 ml of LE90 (a commecially available amyloglucosidase solution (AMB Biochemical, Stockport, England)) was distributed throughout porous titania spheroids (5 ml). A cooled 2% solution (2.25 ml) of tannic acid in acetone, into which a 50% aqueous solution of glutaraldehyde (0.35 ml) had recently been mixed, was added and the resulting stiff slurry thoroughly mixed on an ice bath. After 5 hours the particles were washed and the enzyme activity was assayed, using a solution of dextrin. The enzyme activity was noted as 4.06 mg glucose/ml/min.

EXAMPLE 13

The procedure of Example 12 was repeated with the exception that the precipitating agent used was 10% aqueous tannic acid (pH 4.5, 2.25 ml) in place of tannic acid in acetone. The enzyme activity was noted as 3.24. Comparing the enzyme activities obtained in Examples 12 and 13 it is seen that the use of acetone in the precipitating agent lead to ~20% increase in the immobilized enzyme activity.

I claim:

1. A method for the preparation of discrete particles containing a biologically active substance, comprising discrete particles of porous support material having a biologically active substance immobilised in the pores thereof, which method comprises selecting discrete particles of a porous support material having a pore size and structure that permits entry of a solution containing biologically active substance, said particles also being selected to have a particle size suitable for use in a column or fluidised bed reactor, introducing a solution containing biologically active substance into the pores of said particles of porous support material substantially to fill the pore volume of said particles of porous support material, treating the solution introduced into the pores with a precipitating agent and a cross-linking agent, said treatment with a precipitating agent precipitating said biologically active substance so as to retain said biologically active substance in the pores of the particles of porous support material and thereby hold the biologically active substance available for cross-linking by said cross-linking agent, said precipitating agent being selected from the group consisting of tannic acid in ethanol, tannic acid in acetone, tannic acid in water/isopropanol, a synthetic polyphenol in acetone, a synthetic polyphenol in water/acetone, tannic acid in water/acetone and acetone, and said treatment with a cross-linking agent cross-linking the biologically active substance precipitated in the pores of the porous support material so as to immobilise biologically active substance in the pores of the particles of porous support material, said introduction of solution containing biologically active substance and said precipitating and cross-linking being conducted so as to provide a major proportion of the immobilised biologically active substance in the pores of, rather than on the external surface of, the particles of porous support material.

2. A method as claimed in claim 1 wherein the precipitation and cross-linking are carried out sequentially by treating the solution of the biologically active substance in the pores with the precipitating agent and then treating the precipitated biologically active substance with the cross-linking agent.

3. A method as claimed in claim 2 wherein introducing of the solution containing biologically active substance into the pores of the particles is carried out by soaking the particles in a concentrated solution of biologically active substance to introduce solution into the pores of the porous support material prior to subsequent treatment with the precipitating agent and with a cross-linking agent.

4. A method as claimed in claim 1 wherein the treatment with a precipitating agent and a cross-linking agent is conducted simultaneously and said precipitating occurs before said cross-linking.

5. A method as claimed in claim 1, wherein the biologically active substance is immobilised by being treated with a cross-linking agent selected from the group consisting of glutaraldehyde, formaldehyde, diethylpyrocarbonate, glyoxal and bis-diazonium salt.

6. A method as claimed in claim 1 wherein the particles of support material are selected from the group consisting of porous alumina spheroids, porous zirconia spheroids, controlled pore glass, crushed thermalite block, alumino-silicate catalyst particles, and a porous natural earth.

7. A method as claimed in claim 1 wherein the biologically active substance is an enzyme.

8. A method as claimed in claim 7 wherein the enzyme is amyloglucosidase, lactase, α-amylase, chymotrypsin, trypsin, urease, glucose oxidase, lipoxidase, glucose isomerase, papain, neutrase and pronase.

9. A method as claimed in claim 1 wherein surplus precipitated and cross-linked biologically active substance outside of the particles is removed.

10. Discrete particles of a porous support material having immobilised thereon a biologically active substance, when prepared by a method as claimed in claim 1.

11. A method for the preparation of discrete particles containing a biologically active substance comprising soaking particles of porous support material in a concentrated solution of biologically active substance subjecting said soaked particles to freeze-drying to retain biologically active substance in the particles of porous support material, introducing further biologically active substance into the pores of the particles by immersion in a concentrated solution of biologically active substance, precipitating said further introduced biologically active substance by use of a precipitating agent selected from the group consisting of a water miscible organic liquid and a precipitating agent including a water miscible organic liquid for improving the precipation, and cross-linking biological active substance retained in the pores by said freeze drying and said precipitation by treatment with a cross-linking agent under conditions such that substantially no retained substance goes into solution, to immobilize the biologically active substance in the pores of the particles of the support material.

* * * * *